(12) United States Patent
Tryggvason et al.

(10) Patent No.: US 8,722,405 B2
(45) Date of Patent: *May 13, 2014

(54) COMPOSITION AND METHOD FOR ENABLING PROLIFERATION OF PLURIPOTENT STEM CELLS

(76) Inventors: Karl Tryggvason, Djursholm (SE); Anna Domogatskaya, Rönninge (SE); Sergey Rodin, Stockholm (SE)

( * ) Notice: Subject to any disclaimer, the term of this patent is extended or adjusted under 35 U.S.C. 154(b) by 617 days.

This patent is subject to a terminal disclaimer.

(21) Appl. No.: 11/969,620

(22) Filed: Jan. 4, 2008

(65) Prior Publication Data

US 2008/0213885 A1 Sep. 4, 2008

Related U.S. Application Data

(60) Provisional application No. 60/883,406, filed on Jan. 4, 2007.

(51) Int. Cl.
*C12N 5/00* (2006.01)
*C12N 5/02* (2006.01)
*C12N 5/071* (2010.01)
*C12N 5/07* (2010.01)
*C12N 5/10* (2006.01)

(52) U.S. Cl.
USPC ............................ 435/402; 435/354; 435/366

(58) Field of Classification Search
CPC ........................................................ C12N 5/0606
USPC ........................................ 435/402, 366, 354
See application file for complete search history.

(56) References Cited

FOREIGN PATENT DOCUMENTS

WO  WO 2006/017370 A  2/2006
WO  WO 2008084401     7/2008

OTHER PUBLICATIONS

Greenlea. Toxicology in Vitro, 19: 389-397,2005.*
Lim et al. Proteomics, 2:1187-1203, 2002.*
Appendix F from the NIH website, definition of "Pluripotent Stem cell", accessed online on Feb. 25, 2009.*
Hashimoto et al. Exp. Cell Res., 310: 256-269, 2005.*
Bair et al. Neoplasia, 7(4): 380-389, 2005.*
Beattie et al. Stem Cells, 23: 489-495, 2005.*
"laminin" from Millipore catalog, http://www.millipore.com/, accessed online on Feb. 24, 2009.*
Smith et al. J. of Tiss. Cult. Methods. 13: 89-94, 1991.*
Thomson. Science, 282: 1145-1147, 1998.*
Chu et al. J. Mol. Med., 76: 184-192, 1998.*
Patarroyo et al. Seminars in Cancer Biology, 12: 197-207, 2002.*
Matrigel. BDBiosciences webpage. www.bdbiosciences.com, accessed online on Feb. 25, 2009.*
The Biosciences website, accessed at http://www.biocompare.com/Articles/ProductReview/146/BD-Matrigel-Matrix-Growth-Factor-Reduced-GFR-from-BD-Biosciences.html Jul. 30, 2003, accessed online on Jul. 8, 2010.*
Skottman, H., et al. (2006); The derivation of clinical-grade human embryonic stem cell lines; FEBS Lett 580, 2875-2878.
Williams R.L., et al. (1988); Myeloid leukemia inhibitory factor maintains the developmental potential of embryonic stem cells, Nature Dec. 15, 1988; 336(6200):684-7.
Hovatta, O., and Skottman, H. (2005); Feeder-free derivation of human embryonic stem-cell lines; Lancet 365, 1601-1603.
Richards, M., Fong, et al. (2002); Human feeders support prolonged undifferentiated growth of human inner cell masses and embryonic stem cells; Nat Biotechnol 20, 933-936.
Xu, C., et al. (2001); Feeder-free growth of undifferentiated human embryonic stem cells; Nat Biotechnol 19, 971-974.
Xu, R. H., et al. (2005); Basic FGF and suppression of BMP signaling sustain undifferentiated proliferation of human ES cells; Nat Methods 2, 185-190.
Klimanskaya, I., et al. (2005); Human embryonic stem cells derived without feeder cells; Lancet 365, 1636-1641.
Cooper, A. R., and MacQueen, H. A. (1983); Subunits of laminin are differentially synthesized in mouse eggs and early embryos; Dev Biol 96, 467-471.
Dziadek, M., and Timpl, R. (1985); Expression of nidogen and laminin in basement membranes during mouse embryogenesis and in teratocarcinoma cells; Dev Biol 111, 372-382.
Colognato, H., and Yurchenco, P. D. (2000); Form and function: the laminin family of heterotrimers; Dev Dyn 218, 213-234.
Aumailley, M., et al. (2005); A simplified laminin nomenclature; Matrix Biol 24, 326-332.
Kortesmaa, J., et al. (2000); Recombinant laminin-8 (alpha(4)beta(1)gamma(1)). Production, purification, and interactions with integrins. J Biol Chem 275, 14853-14859.
Doi, M., et al. (2002); Recombinant human laminin-10 (alpha5beta1gamma1); Production, purification, and migration-promoting activity on vascular endothelial cells. J Biol Chem 277, 12741-12748.
Wartiovaara, J. et al. (2004); Nephrin strands contribute to a porous slip diaphragm scaffold as revealed by electron tomography. J. Clin. Invest. 114: 1476-1483 (2004).
Tryggvason, K et al. (2006); Mechanisms of Disease: Hereditary Proteinuria Syndromes and Mechanisms of Proteinuria. N Engl J Med, vol. 354: 1387-1407 (Mar. 30, 2006).
Hudson, B.G. et al. (2003); Mechanisms of Disease: Alport's Syndrome, Goodpasture's Synhdrome, and Type IV Collagen. N Engl J Med, vol. 348: 2543-2556 (Jun. 19, 2003).
Wondimu, Z et al. (2005); Characterization of commercial laminin preparations from human placenta in comparison to recombinant laminins 2 ($\alpha 4\beta 1_\gamma 1$), 10 ($\alpha 5\beta 1_\gamma 1$). Matrix Biology 25 (2006) 89-93.

(Continued)

*Primary Examiner* — Thaian N Ton
(74) *Attorney, Agent, or Firm* — Richard M. Klein; Fay Sharpe LLP

(57) ABSTRACT

The present disclosure is directed to the development of compositions, such as extracellular matrices, and processes for using the same, for culturing stem cells in vitro in an undifferentiated state. In this regard, it has been discovered that when pluripotent mouse and human embryonic stem cells are cultured on plates coated with recombinant laminin-10 (laminin-511) or laminin-5 (laminin-322), or their functional domains, the embryonic stem cells proliferated and maintained their pluripotency.

3 Claims, 12 Drawing Sheets

(56) References Cited

OTHER PUBLICATIONS

Hashimoto et al., "Regulation of proliferation and chondrogenic differentiation of human mesenchymal stem cells by laminin-5 (laminin-332)", Stem Cells (Miamisburg), vol. 24, No. 11. Nov. 2006, pp. 2346-2354.

Mallon et al., "Toward xeno-free culture of human embryonic stem cells", International Journal of Biochemistry and Cell Biology (Exeter, GB), vol. 38, No. 87. Jan. 1, 2006, pp. 1063-1075.

Domogatskaya et al., "Laminin-511 but not -332, -111, or -411 enables mouse embryonic stem cell self-renewal in vitro", Stem Cells (Dayton, Ohio), Nov. 2008, vol. 26, No. 11, Nov. 2008, pp. 2800-2809.

International Search Report dated Dec. 16, 2008.

Domogatskaya, Anna et al., "Laminin-511 but no -322, -111, or -411 enables mouse embryonic stem cell self-renewal in vitro" Stem Cells, Alphamed Press LNKD-DOI: 10.1634/Stemcells. 2007-0389, vol. 26, No. 11. pp. 2800-2809.

Meng Guoliang, et al., A novel method for generating xeno-free human feeder cells for human embryonic stem cell culture: Stem Cells and Development, Elsevier, NL LNKD-DOI:10.1089/SCD. 2007.0236, vol. 17, No. 3. pp. 413-422.

Ludwig, T. E., et al., "Derivation of human embryonic stem cells in defined conditions" Nature Biotechnology, Feb. 2006 Nature Publishing Group US, vol. 24, No. 2. pp. 185-187.

Miyazaki, T., et al., "Recombinant human laminin isoforms can support the undifferentiated growth of human embryonic stem cells" Biochemical and Biophysical Research Communications, Academic Press Inc., Orlando, FL, US LNKD-DOI:10.1016/J.BBRC.2008.07. 111, vol. 375, No. 1. pp. 27-32.

Rodin, Sergey, et al., "Long-term self-renewal of human pluripotent stem cells on human recombinant laminin-511." Nature Biotechnology, Jun. 2010 LNKD-PUBMED: 20512123, vol. 28, No. 7. pp. 611-615.

International Search Report dated Jun. 30, 2010.

* cited by examiner

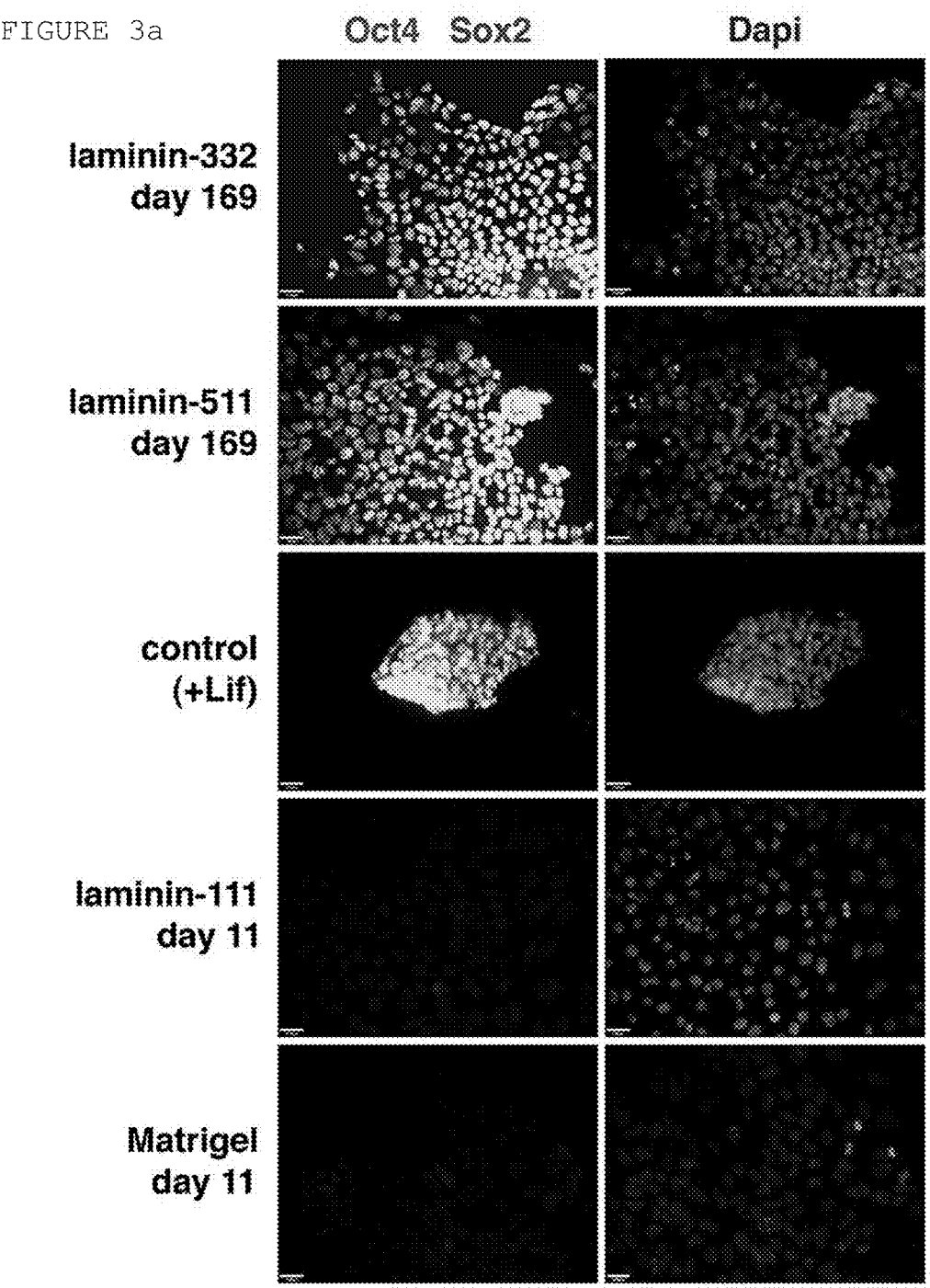

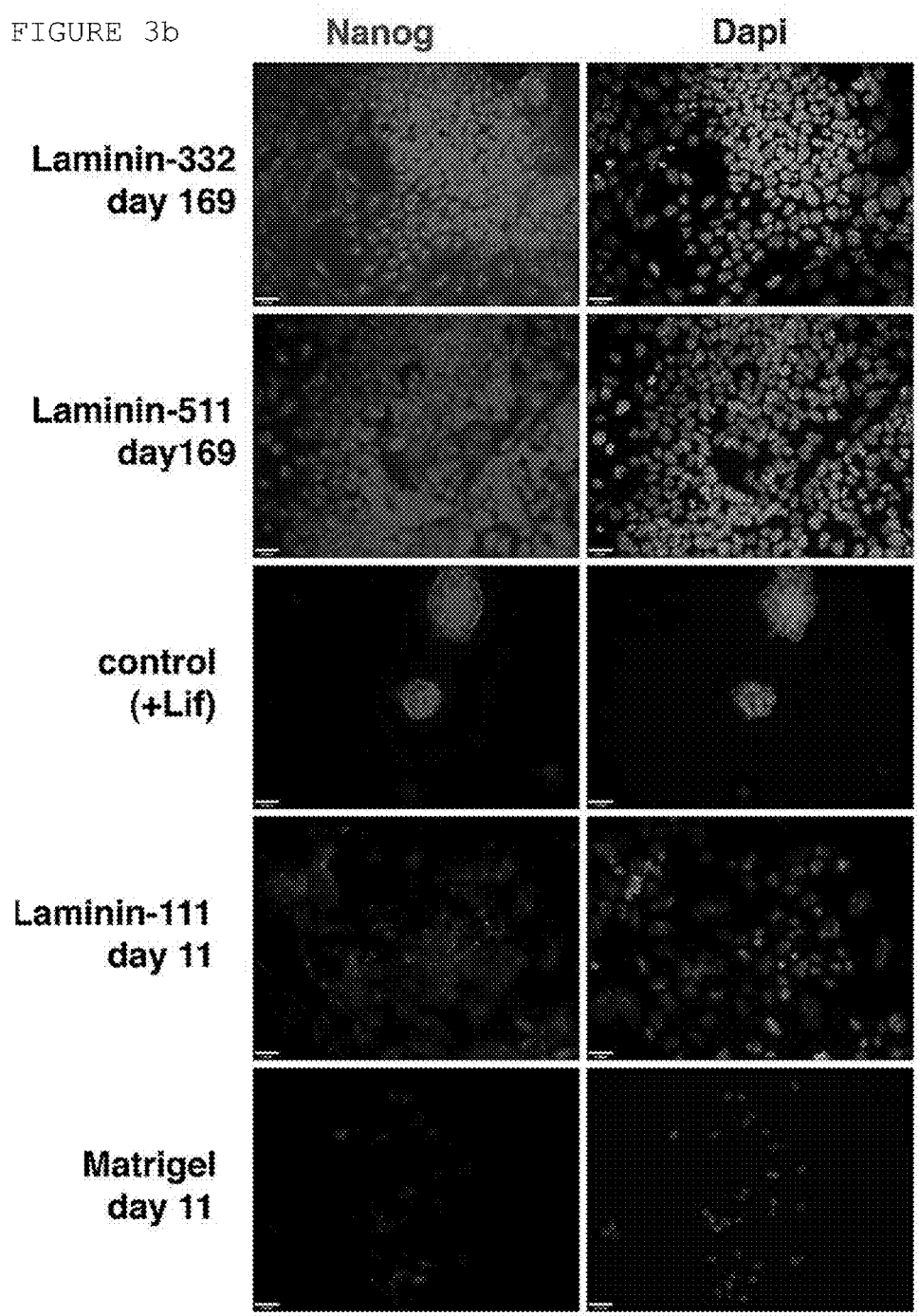

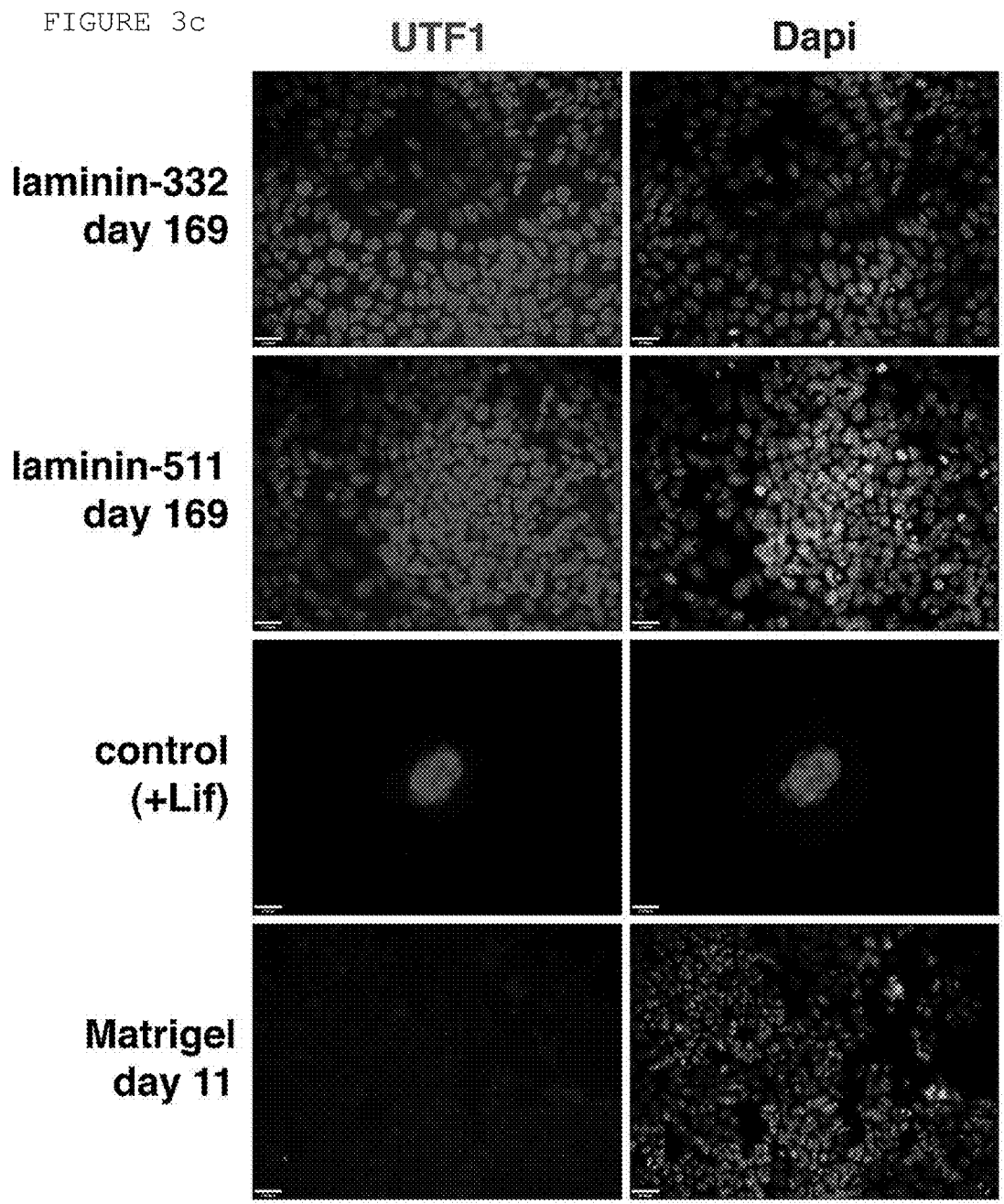

COMPOSITION AND METHOD FOR ENABLING PROLIFERATION OF PLURIPOTENT STEM CELLS

CROSS REFERENCE TO RELATED APPLICATIONS

This application claims priority to U.S. Provisional Application Ser. No. 60/883,406, filed on Jan. 4, 2007, which is fully incorporated herein by reference.

BACKGROUND

The present disclosure relates, in various exemplary embodiments, generally to compositions and methods for enabling adhesion, proliferation and self-renewal maintenance of pluripotent, or undifferentiated, stem cells in vitro. These stem cells include embryonic stem cells, such as murine or human, and bone marrow stem cells.

A stem cell is an undifferentiated cell from which specialized cells are subsequently derived. Embryonic stem cells possess extensive self-renewal capacity and pluripotency with the potential to differentiate into cells of all three germ layers. They are useful for therapeutic purposes and may provide unlimited sources of cells for tissue replacement therapies, drug screening, functional genomics and proteomics. (Skottman, H., Dilber, M. S., and Hovatta, O. (2006); The derivation of clinical-grade human embryonic stem cell lines; FEBS Lett 580, 2875-2878).

Murine pluripotent embryonic cells can be maintained in a pluripotent state in in vitro cell culture conditions in the presence of Leukemia Inhibitory Factor (LIF). (Williams R L, Hilton D J, Pease S, Willson T A, Stewart C L, Gearing D P, Wagner E F, Metcalf D, Nicola N A, Gough N M (1988); Myeloid leukemia inhibitory factor maintains the developmental potential of embryonic stem cells, Nature 1988 Dec. 15; 336(6200):684-7).

Additionally, murine pluripotent embryonic cells can be maintained in a pluripotent state in vitro when cultured on mouse embryonic fibroblasts as feeder cells. Human embryonic cells also require feeder cells for maintenance in a pluripotent state in vitro or differentiation inhibitors like Noggin and/or high doses of basic fibroblast growth factor (FGF) when cultured on Matrigel™ (see for review: Skottman, H., Dilber, M. S., and Hovatta, O. (2006); The derivation of clinical-grade human embryonic stem cell lines; FEBS Lett 580, 2875-2878). However, the use of feeder cells has a number of drawbacks. For example, feeder cells can contain pathogens, such as viruses that can infect the stem cells (Hovatta, O., and Skottman, H. (2005); Feeder-free derivation of human embryonic stem-cell lines; Lancet 365, 1601-1603; Skottman, H., Dilber, M. S., and Hovatta, O. (2006); The derivation of clinical-grade human embryonic stem cell lines; FEBS Lett 580, 2875-2878).

Feeder-free systems that support human embryonic stem cell self-renewal require either i) Matrigel™ (Richards, M., Fong, C. Y., Chan, W. K., Wong, P. C., and Bongso, A. (2002); Human feeders support prolonged undifferentiated growth of human inner cell masses and embryonic stem cells; Nat Biotechnol 20, 933-936); (Xu, C., Inokuma, M. S., Denham, J., Golds, K., Kundu, P., Gold, J. D., and Carpenter, M. K. (2001); Feeder-free growth of undifferentiated human embryonic stem cells; Nat Biotechnol 19, 971-974); (Xu, R. H., Peck, R. M., Li, D. S., Feng, X., Ludwig, T., and Thomson, J. A. (2005); Basic FGF and suppression of BMP signaling sustain undifferentiated proliferation of human ES cells; Nat Methods 2, 185-190); or, ii) mouse feeders-derived extracellular matrix (Klimanskaya, I., Chung, Y., Meisner, L.; Johnson, J., West, M. D., and Lanza, R. (2005); Human embryonic stem cells derived without feeder cells; Lancet 365, 1636-1641) as adhesive substrata. However, these coatings are of xenogenic origin and therefore cannot be used in clinics according to FDA requirements (Hovatta, O., and Skottman, H. (2005); Feeder-free derivation of human embryonic stem-cell lines; Lancet 365, 1601-1603). These coatings also fail to fulfill criteria of defined system and non-immunogenicity, importance of which is discussed in (Hovatta, O., and Skottman, H. (2005); Feeder-free derivation of human embryonic stem-cell lines; Lancet 365, 1601-1603; Skottman, H., Dilber, M. S., and Hovatta, O. (2006); The derivation of clinical-grade human embryonic stem cell lines; FEBS Lett 580, 2875-2878).

During mammalian embryonic development, a fertilized oocyte first divides into two cells, followed by another cell duplication to generate a four-cell embryo. At the four-cell stage, the embryonic cells are bound together with the help of cell membrane proteins and also the molecules of a new connective tissue (extracellular matrix). The first extracellular matrix molecules to appear are basement membrane proteins, such as laminin and proteoglycan (Cooper, A. R., and MacQueen, H. A. (1983); Subunits of laminin are differentially synthesized in mouse eggs and early embryos; Dev Biol 96, 467-471) (Dziadek, M., and Timpl, R. (1985); Expression of nidogen and laminin in basement membranes during mouse embryogenesis and in teratocarcinoma cells; Dev Biol 111, 372-382). Subsequently, the embryonic cells start to differentiate into the three germ cell layers; ectoderm, endoderm and mesoderm, with initiation of morphogenesis. The extracellular matrix molecules, such as laminins are responsible for interactions with cell surface receptors, thus regulating cell behavior such as adhesion, proliferation, migration and differentiation (Colognato, H., and Yurchenco, P. D. (2000); Form and function: the laminin family of heterotrimers; Dev Dyn 218, 213-234), while other extracellular matrix components such as collagens of types I, II, III or IV primarily serve a mechanical supportive function (Aumailley, M., and Gayraud, B. (1998); Structure and biological activity of the extracellular matrix; J Mol Med 76, 253-265).

Extracellular matrix derived from murine fibroblasts, in combination with soluble differentiation inhibitors may be an adequate replacement for feeder cells (Klimanskaya, I., Chung, Y., Meisner, L., Johnson, J., West, M. D., and Lanza, R. (2005); Human embryonic stem cells derived without feeder cells; Lancet 365, 1636-1641), which demonstrates the critical role of extracellular matrix molecules. Laminins are large trimeric extracellular matrix proteins that are composed of alpha, beta, and gamma chains. There exist five different alpha chains, three beta chains and three gamma chains that in mouse and human tissues have been found in at least fifteen different combinations (Colognato, H., and Yurchenco, P. D. (2000); Form and function: the laminin family of heterotrimers; Dev Dyn 218, 213-234); (Aumailley, M., Bruckner-Tuderman, L., Carter, W. G., Deutzmann, R., Edgar, D., Ekblom, P., Engel, J., Engvall, E., Hohenester, E., Jones, J. C., et al. (2005); A simplified laminin nomenclature; Matrix Biol 24, 326-332). These molecules are termed laminin-1 to laminin-15 based on their historical discovery, but an alternative nomenclature describes the isoforms based on their chain composition, e.g. laminin-111 (laminin-1) that contains alpha-1, beta-1 and gamma-1 chains (laminin nomenclature: (Aumailley, M., Bruckner-Tuderman, L., Carter, W. G., Deutzmann, R., Edgar, D., Ekblom, P., Engel, J., Engvall, E., Hohenester, E., Jones, J. C., et al. (2005); A simplified laminin nomenclature; Matrix Biol 24, 326-332)).

Notwithstanding the above, there continues to be a need for providing compositions and methods for culturing and growing embryonic stem cells. In this regard, providing compositions and methods for enabling the proliferation and survival of pluripotent stem cells in vitro without use of differentiation inhibitory agents such as LIF or feeder cells would be advantageous.

SUMMARY

The present disclosure is directed to the development of compositions, such as extracellular matrices, and processes for using the same, for culturing stem cells in vitro in an undifferentiated state. Preferably, the stem cells are embryonic stem cells, such as murine or human embryonic stem cells. However, the present disclosure also includes the use of bone marrow stem cells as well.

It has been found that certain laminins provide a defined and suitable extracellular matrix for the growth and proliferation of undifferentiated mouse and human embryonic stem cells in vitro. This is absent any feeder cells and/or differentiation inhibitors. For example, it has been discovered that when pluripotent mouse embryonic stem cells are cultured on plates coated with recombinant laminin-10 (laminin-511) or laminin-5 (laminin-332), the embryonic stem cells proliferate and maintain their pluripotency even in an absence of differentiation inhibitors.

Also, it has been found that when pluripotent human embryonic stem cells are cultured on plates coated with recombinant laminin-10 (laminin-511) in a chemically defined medium, such as an analog of mTeSR1, the cells can proliferate and maintain their pluripotency even in an absence of differentiation inhibitors.

These and other non-limiting features of the present disclosure are discussed in more detail below.

BRIEF DESCRIPTION OF THE DRAWINGS

The following is a brief description of the drawings, which are presented for the purposes of illustrating the exemplary embodiments disclosed herein and not for the purposes of limiting the same.

FIGS. 3a-3d relate to a series of color photomicrographs (Immunofluorescence (×40)) demonstrating mouse embryonic stem cell self-renewal effect on laminins-332 and -511. FIG. 3a is directed to photomicrographs of immunofluorescence staining against pluripotency markers Oct4 and Sox2. Embryonic stem cells cultured in presence of LIF (control+LIF) express pluripotency marker Oct4 and Sox2 (control). After culturing on laminin-332 or laminin-511 in absence of LIF or any other differentiation inhibitor for 169 days, embryonic stem cells continue to express Oct4 and Sox2. It is noteworthy that after culturing for only 11 days on laminin-111 or on Matrigel™, embryonic stem cells cease to express Oct4 and Sox2. FIG. 3b relates to photomicrography showing similar data of immunofluorescence staining against pluripotency marker Nanog. FIG. 3c shows similar data of immunofluorescence staining against pluripotency marker UTF1. FIG. 3d is directed to photomicrographs of immunofluorescence staining against pluripotency marker Oct4 and differentiation marker Collagen IV.

DETAILED DESCRIPTION

Figure 1A:
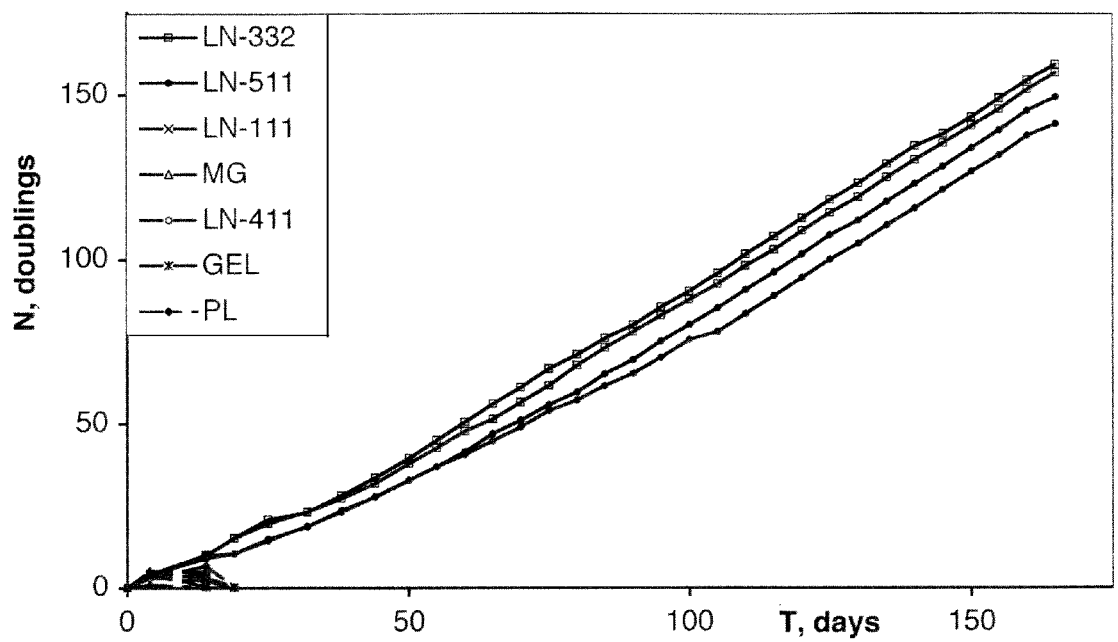
FIG. 1a is a graph showing the proliferation of mouse embryonic stem cells on laminins (LN), Matrigel™ (MG), gelatin (GEL) and poly-D-lysine (PL). Cells expanded on LN-332 and LN-511 for up to at least 169 days during which about 150 doublings in cell number occurred. In contrast, the cells did not self-renew on LN-111, LN-411, gelatin or poly-D-lysine.
Figure 5A:
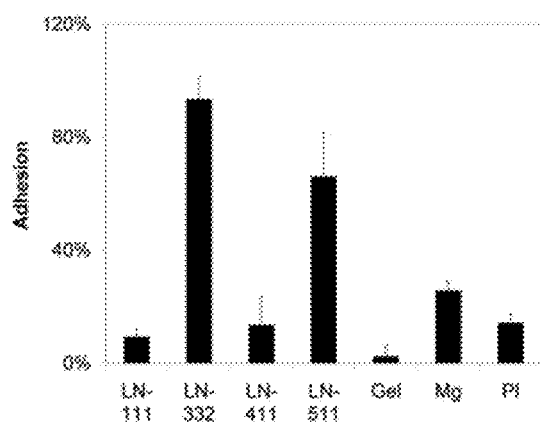
FIG. 5a is a graph showing adhesion of pluripotent mouse embryonic stem cells to different coating surfaces: laminin-111 (LN-111), laminin-332 (LN-332), laminin-411 (LN-411), laminin-511 (LN-511), Matrigel (MG), gelatin (GEL) and poly-D-lysin (PL). Values are shown as percentage of attached cells±standard deviation (STD).
Figure 5B:
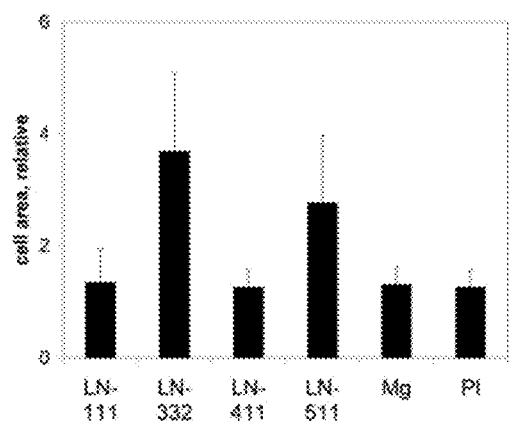
FIG. 5b is a graph showing spreading of pluripotent ESCs adhered to different coating surfaces. The area of cells that adhered to a certain coating was calculated as a measure of spreading efficacy. The areas are depicted as average relative areas±standard deviation (STD).
Figure 5C:
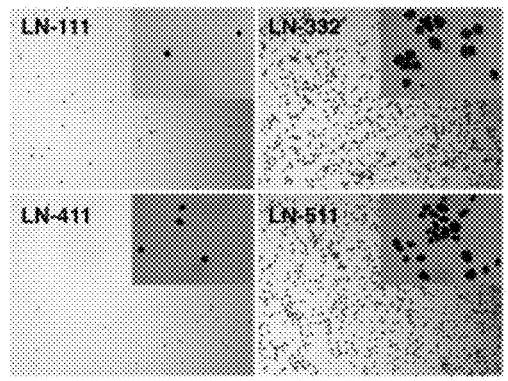
FIG. 5c is a series of four (4) micrographs showing embryonic stem cells adherent to different laminins after 1 hour incubation. Crystal violet staining, magnification (×5/×40). As indicated, laminin-332 and -511, unlike laminins-111 or -411, are highly adhesive for embryonic stem cells.
Figure 6:
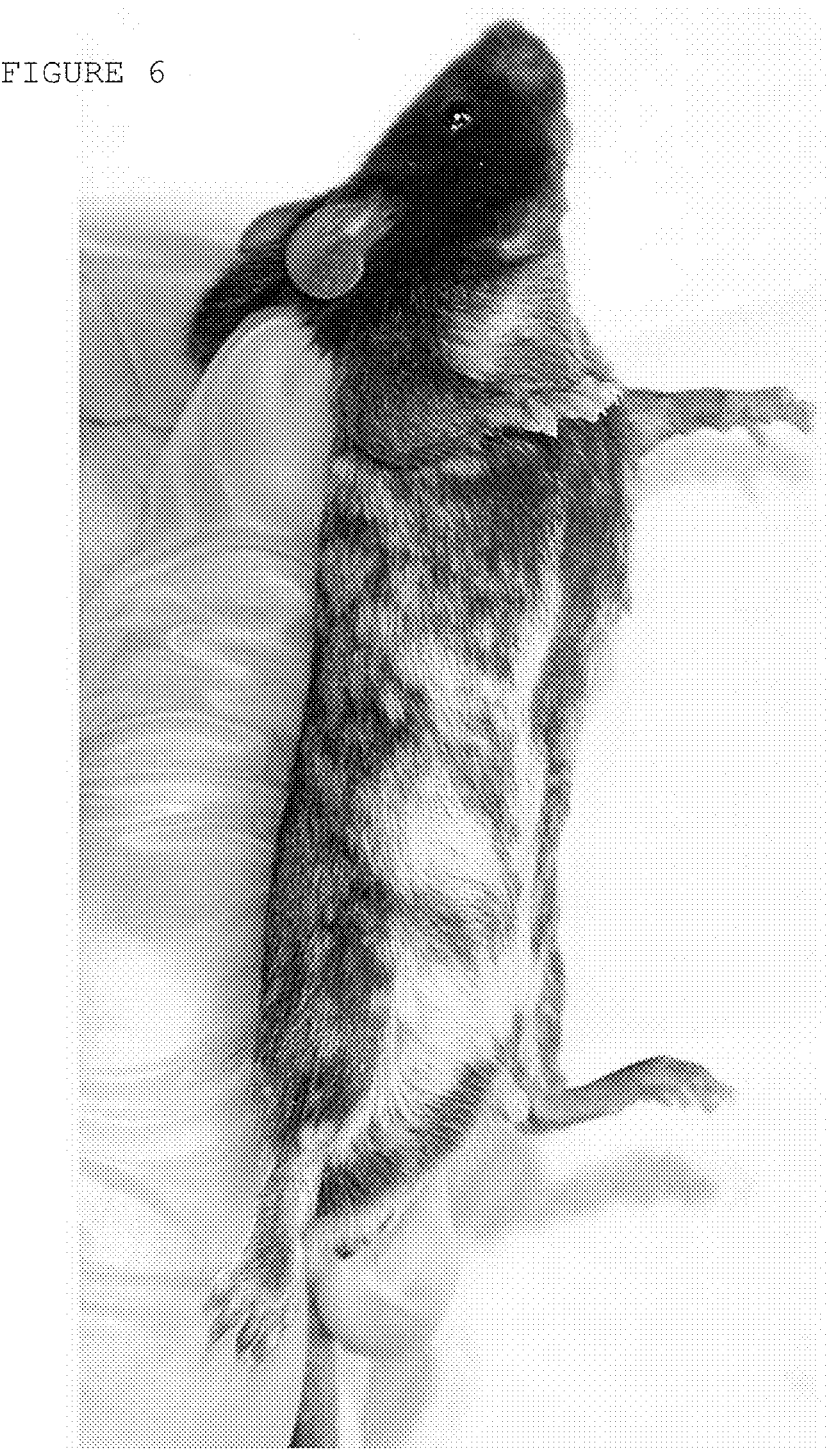
FIG. 6 is a photograph of a chimeric mouse derived from mouse embryonic stem cells cultured on laminin-511 for 3 months in absence of feeders and any differentiation inhibitors.

It has been found that when pluripotent mouse embryonic stem cells are cultured on plates coated with recombinant human laminin-5 (laminin-332) or laminin-10 (laminin-511) in the presence of mitogenic factor bFGF (10 ng/ml) and in the absence of any differentiation inhibitors, the cells proliferate and maintain their pluripotency for at least 140 days (23 passages) (FIG. 1a, FIG. 6). Expression of pluripotency markers, such as Oct4, TERT, Sox2, Nanog and UTF1 (FIG. 2, FIGS. 3a-3d, FIG. 4), and the proliferation rate (FIG. 1a), also remained stable. Furthermore, it was noted that the adhesion of embryonic cells to laminin-5 or laminin-10 molecules correlated with ability of the latter to sustain embryonic cells cell self-renewal (FIGS. 5a-5c).

Figure 1B:
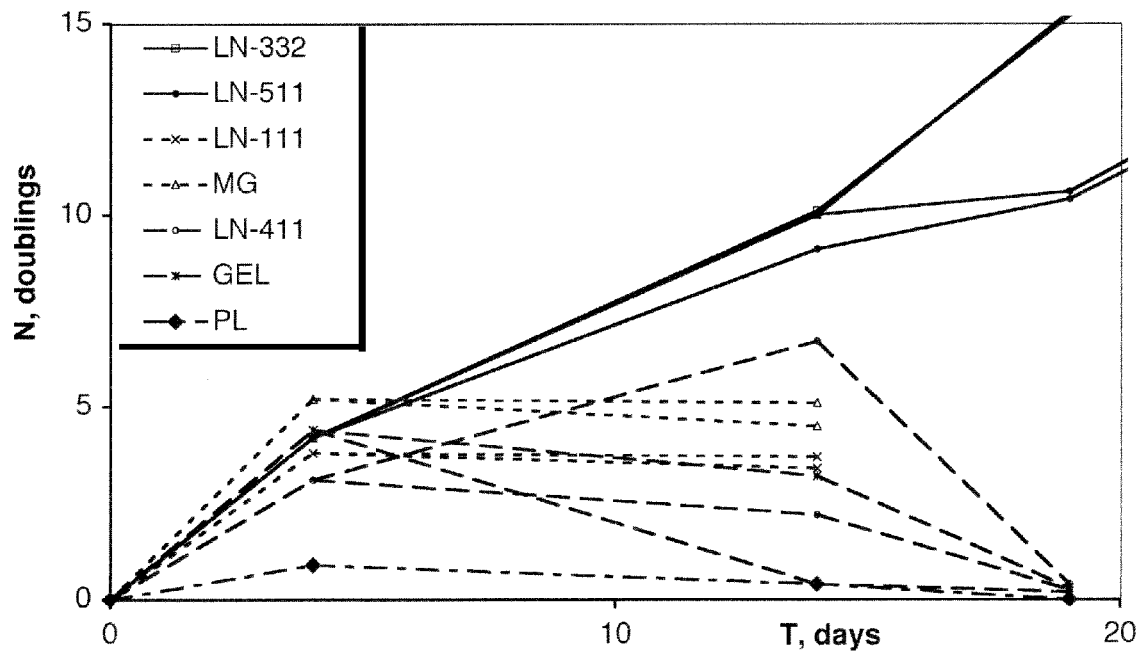
FIG. 1b is a graph showing magnification of days 1-20 in FIG. 1a, showing that the cells proliferated to a certain limit on LN-111, LN-411, Matrigel™ and gelatin, but proliferation ceased within 1-2 weeks. The cells attached poorly to poly-D-lysine.
Figure 2:
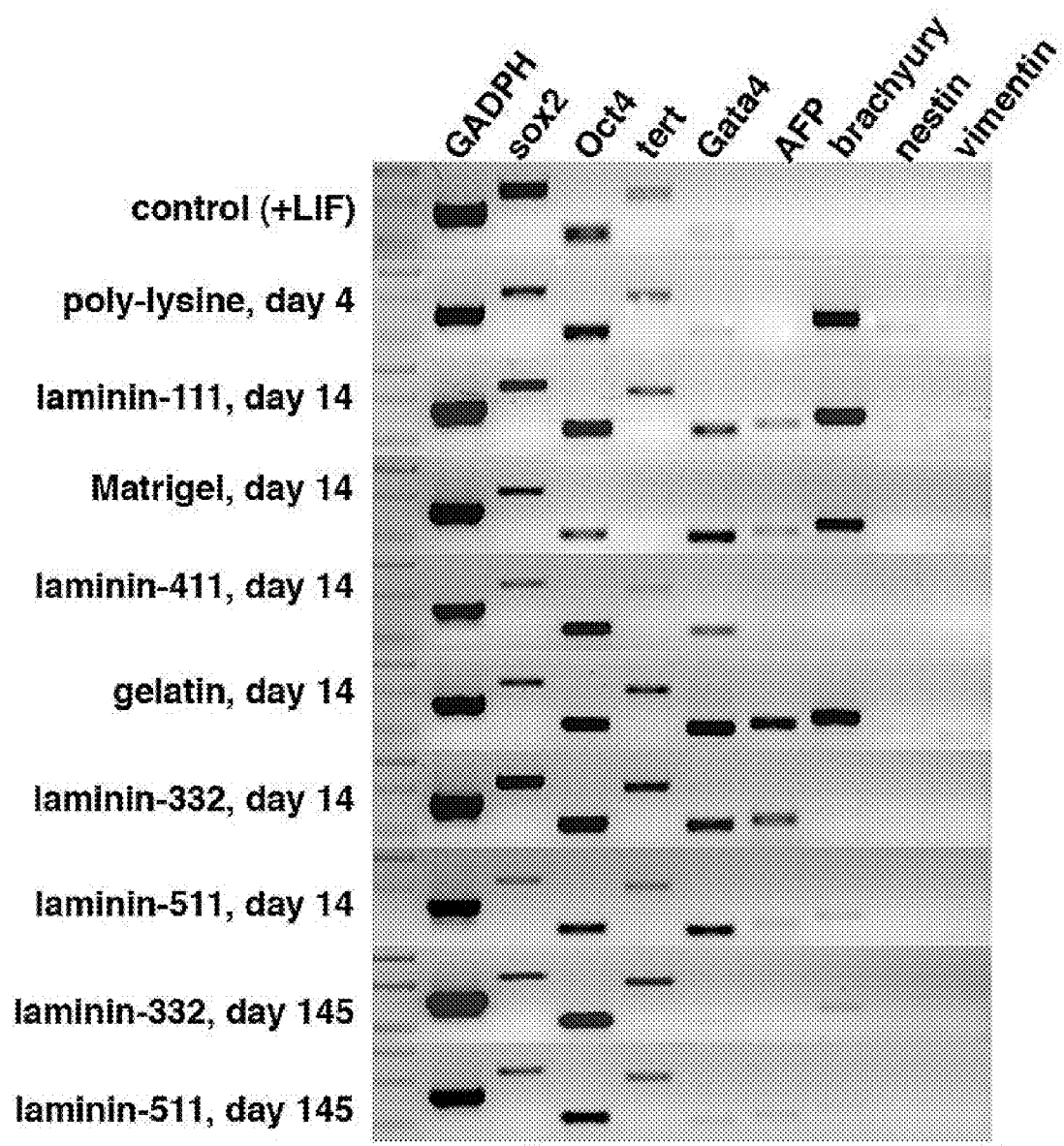
FIG. 2 is a photograph of RT-PCR showing the expression of pluripotency markers (Sox2, Oct4), proliferation marker (Tert) and differentiation markers (alpha-fetoprotein, brachyury, nestin and vimentin) in mouse embryonic stem cells cultured on laminins-111, -312, -411, -511, Matrigel™, gelatin and poly-D-lysine in absence on any differentiation factors or differentiation inhibitors for up to 145 days.
Figure 3D:
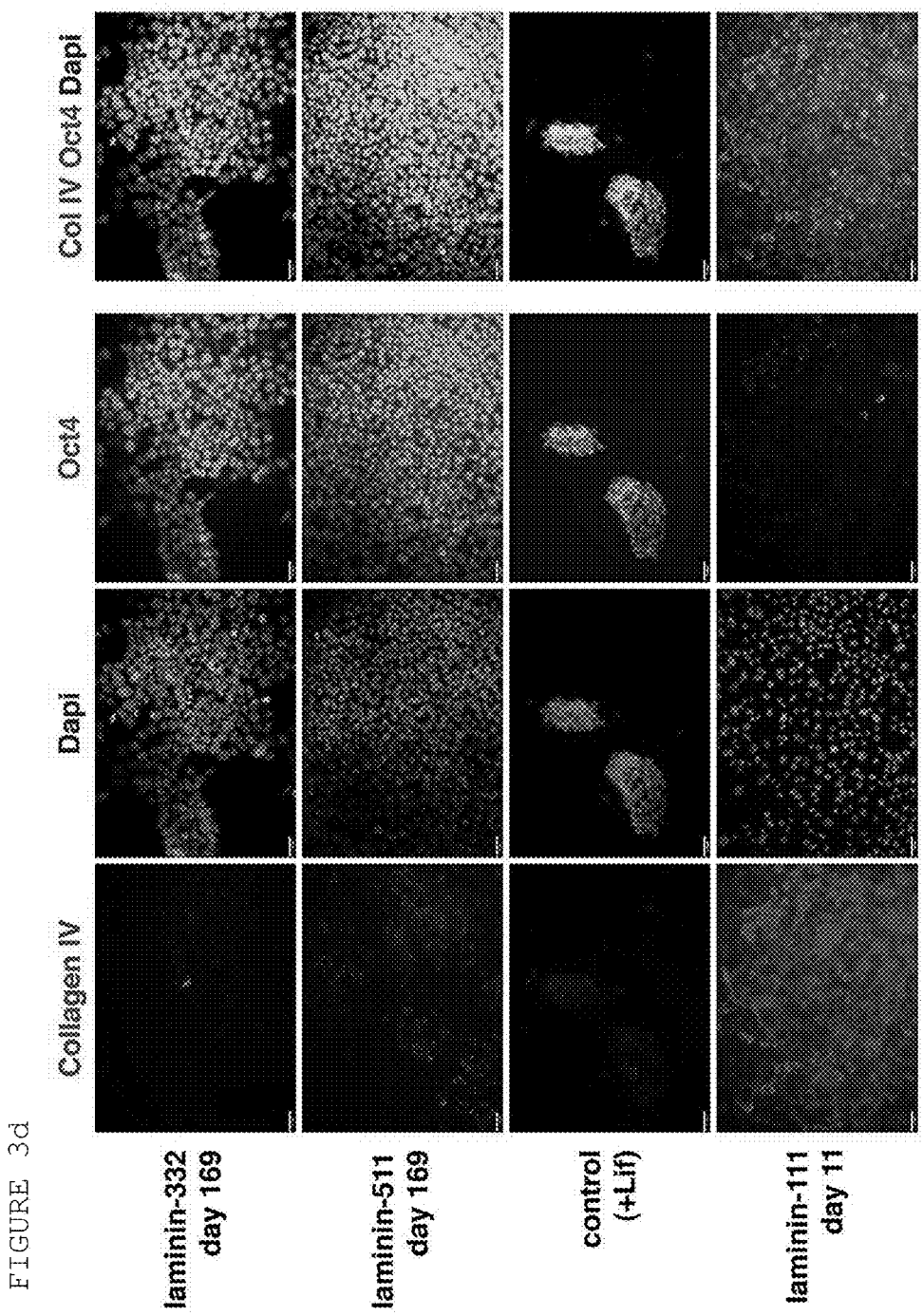
Figure 4:
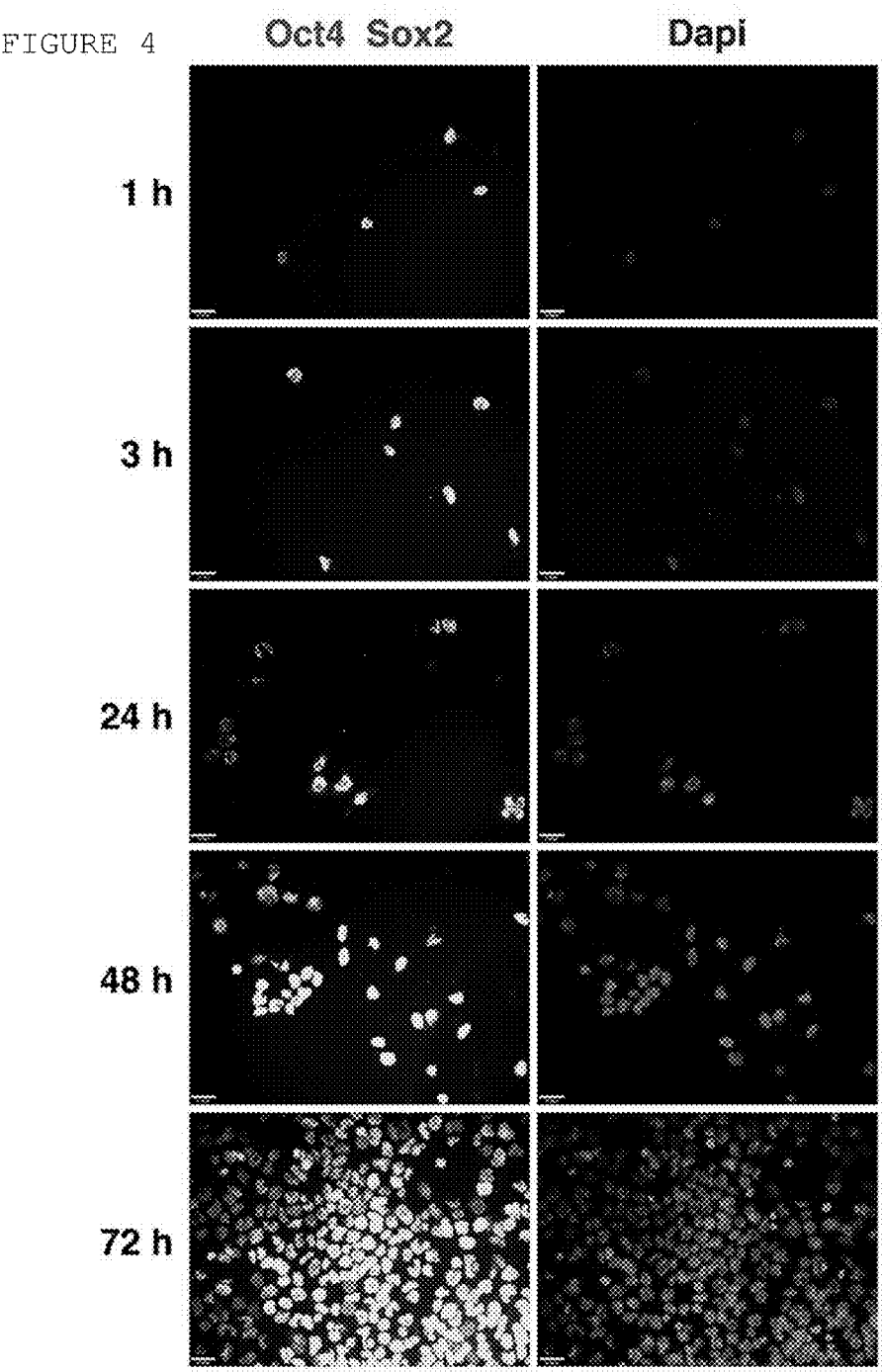
FIG. 4 is a series of color photomicrographs (Immunofluorescence (×40)) demonstrating the mechanism of mouse embryonic stem cell pluripotency maintenance when cultured on laminin-511 in absence of LIF or any other differentiation inhibitor. Embryonic stem cells cultured on laminin-511 in absence of differentiation inhibitors for 80 days, plated at cell density 180 cell/mm$^2$. Photomicrographs were taken in intervals: 1 hour, 3 hours, 1 day, 2 days and 3 days. Pluripotency marker Sox2 is expressed at the same level though during first 2 days. Embryonic stem cells are not in contact with each other, but only contact laminin-511.

In contrast, when the mouse embryonic stem cells were cultured under the same conditions on plates coated with mouse (EHS) laminin-1 (laminin-111), laminin-8 (laminin-411), Matrigel™ or gelatin, the pluripotent cells ceased proliferation after 1-2 weeks (FIG. 1b). They differentiated, or detached, or died. Additionally, cells cultured under these conditions on laminin-111 or Matrigel™ start to express differentiation markers such as collagen IV and brachyury and cease expression of pluripotency markers Oct4, Sox2, Nanog or UTF1 (FIG. 2, FIGS. 3a-3d).

Figure 7:
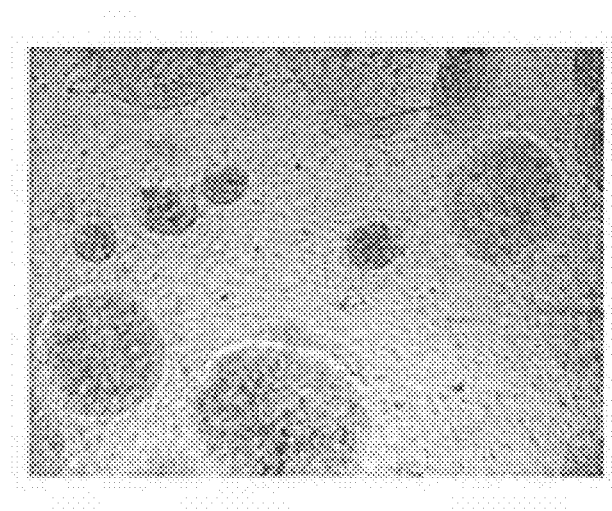
FIG. 7 is a microphotograph (phase contrast) of human embryonic stem cells on plates coated with recombinant laminin-10 (laminin-511) in a chemically defined medium after 105 days of feeder-free culturing.
Figure 8:
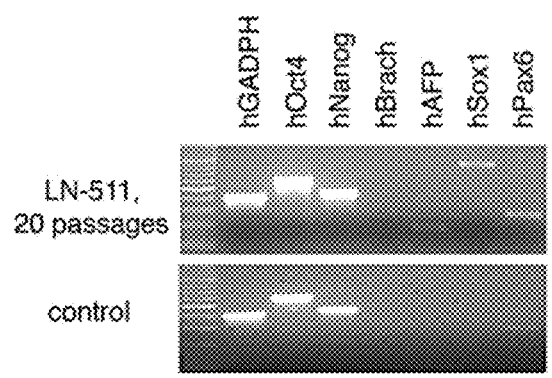
FIG. 8 is a photograph of RT-PCR showing the expression of pluripotency markers (Oct4, Nanog), internal control (GAPDH) and differentiation markers (alpha-fetoprotein, brachyury, Sox1 and Pax6) in human embryonic stem cells cultured on laminin-10 (laminin-511) in the chemically defined medium for 105 days (LN-511, 20 passages) and on human foreskin fibroblasts (control) in the conventional medium. Here, hGADPH, hOct4, hNanog, hBrach, hAFP, hSox1 and hPax6 stand for GAPDH, Oct4, Nanog, brachyury, alpha-fetoprotein, Sox1 and Pax6, respectively.
Figure 9:
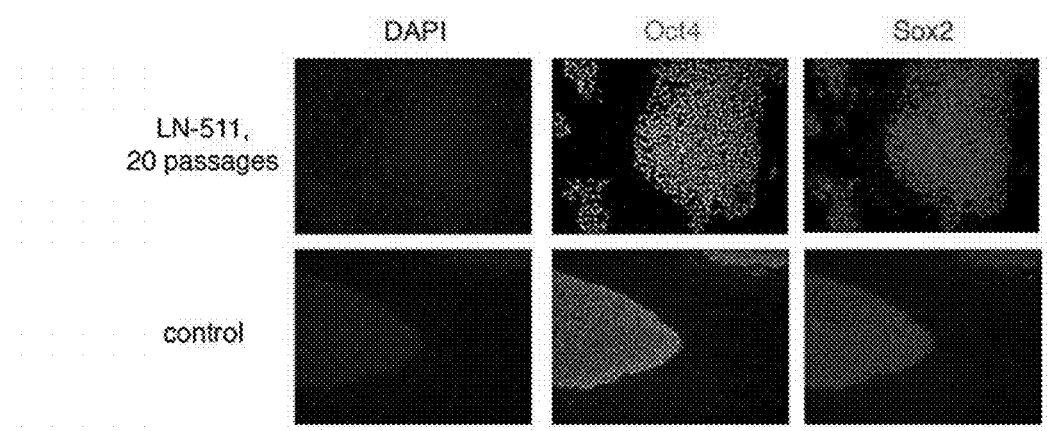
FIG. 9 contains a series of color microphotographs (immunofluorescence) demonstrating human embryonic stem cell self-renewal effect on laminins-511. After culturing on laminin-511 in the chemically defined media for 105 days (20 passages), human embryonic stem cells continue to express pluripotency markers Oct4 (green) and Sox2 (red) (LN-511, 20 passages). Human embryonic stem cells cultured on human foreskin fibroblasts in the conventional medium also express pluripotency markers Oct4 and Sox2 (control).

Also, it has been found that when pluripotent human embryonic stem cells are cultured on plates coated with recombinant human laminin-10 (laminin-511) in chemically defined medium, the cells proliferate and maintain their pluripotency for at least 105 days (20 passages) (FIGS. 7-9). Expression of pluripotency markers, such as Oct4, Sox2 and Nanog, and the proliferation rate, also remained stable.

The present disclosure will further be illustrated in the following non-limiting working examples, it being understood that these examples are intended to be illustrative only and that the disclosure is not intended to be limited to the materials, conditions, process parameters and the like recited herein. All proportions are by weight unless otherwise indicated.

Methods

Cell Culture

Mouse embryonic stem cells (two lines were used: line GSI-1 derived from 129SvJ mice, provided by Uppsala University Transgenic Facility and line RW4) were cultured on extracellular matrix coatings in medium containing 80% Dulbecco's modified Eagle's medium (DMEM), containing GlutaMax-1 and 4.5 g/liter glucose, 20% embryonic cells qualified fetal serum, 1% penicillin, 1% streptomycin, 10 mM Hepes buffer, 1 mM sodium pyruvate, non-essential aminoacids (all provided by Invitrogen), 0.1 mM beta-mercaptoethanol (Sigma) and 10 ng/ml beta fibroblast-growth factor (bFGF) (Chemicon) at 37° C., 5% $CO_2$. Embryonic cells were plated upon extracellular matrix coatings in initial density of 300 cells/$mm^2$. Cells were split once in 4-6 days by 0.05% trypsin-EDTA solution and plated at cell density of 180 cells/$mm^2$. Embryonic cells were cultured as two separate lines on each coating. Cells were counted during each passage using hematocytometer.

Human embryonic stem cells (two lines were used: HS420 and HS207, both kindly provided by Prof. Hovatta, Karolinska University Hospital Huddinge, Karolinska Institute, Sweden) were cultured on plates coated with recombinant laminin-10 (laminin-511) in the chemically defined medium, analog of mTeSR1. The medium was prepared as described in (Ludwig, T. E., Bergendahl, V., Levenstein, M. E., Yu, J., Probasco M. D. and Thomsom, J. A. (2006); Feeder-independent culture of human embryonic stem cells; Nat Methods 8, 637-646) with several exceptions. Firstly, recombinant human FGF basic (R@DSystems) was used instead of zbFGF and albumin from bovine serum (SIGMA-Aldrich, B4287) was used instead of BSA fraction V. Secondly, Insulin-Transferrin-Selenium Supplement (Invitrogen) added in already made medium was used as a source of the elements instead of the method described in the article. The human embryonic stem cells were passages in clumps at 4-6 days intervals by exposure to TrypLE™ Express (GIBCO). The cells were subjected to the enzyme for 2 minutes at room temperature, then washed 2 times with the medium, followed by gentle scraping to collect. Big clumps of the cells were broken by gentle pipetting and 1:3 passaged.

Control human embryonic stem cells were maintained on human foreskin fibroblasts in the conventional medium as described in (Inzunzaa, J., Gertow, K., Strömberg, M., A., Matilainen, E., Blennow, E., Skottman, H., Wolbank, S., Ährlund-Richter, L. and Hovatta, O. (2005); Derivation of Human Embryonic Stem Cell Lines in Serum Replacement Medium Using Postnatal Human Fibroblasts as Feeder Cells. Stem Cells 2005; 23:544-549). The cells were mechanically passaged by cutting the colony to eight pieces using a scalpel under the stereo microscope. Mechanical splitting was carried out at 6-day intervals. Nondifferentiated cells, as judged by morphology, were chosen for each further passage.

Plate Coating 96-well tissue cell culture plates (Sarstedt) were coated overnight at 4° C. by sterile solutions of extracellular matrix proteins: murine laminin-111 (Invitrogen), human recombinant laminin-332, human recombinant laminin-411 (Kortesmaa, J., Yurchenco, P., and Tryggvason, K. (2000); Recombinant laminin-8 (alpha(4)beta(1)gamma(1)). Production, purification, and interactions with integrins. J Biol Chem 275, 14853-14859, U.S. Pat. No. 6,638,907), human recombinant laminin-511 (Doi, M., Thyboll, J., Kortesmaa, J., Jansson, K., Iivanainen, A., Parvardeh, M., Timpl, R., Hedin, U., Swedenborg, J., and Tryggvason, K. (2002); Recombinant human laminin-10 (alpha5beta1gamma1); Production, purification, and migration-promoting activity on vascular endothelial cells. J Biol Chem 277, 12741-12748; U.S. Pat. No. 6,933, 273), all in concentration 30 ug/ml (5 ug/$mm^2$), growth factor-depleted Matrigel™ (1:30) (BD Biosciences), bovine gelatin 1 mg/ml (Sigma), 0.1 mg/ml poly-D-lysine (Sigma).

Cell Adhesion Assays

Attachment assay was performed as described ([Extracellular Matrix Protocols, 2000). Briefly, MaxiSorp 96-well plates (Nunc) coated by extracellular matrix proteins as described above and blocked by 1% heat-denatured BSA solution. Undifferentiated embryonic cells were plated at cell density of 800 cell/$mm^2$ upon extracellular matrix-coated plates and were left to adhere for 1 hour at 37° C. Non-adherent cells were washed away, and adherent cells were fixed for 20 min by 5% glutaraldehyde, stained by 0.1% Crystal Violet.

RT-PCR:

Total RNA was isolated using Absolutely RNA Microprep Kit (Stratagene) according to the manufacturer's instructions from both mouse and human samples. cDNA was synthesized using 0.2 ug of total RNA in 20 ul reaction mixture, containing oligo(dT)12-18 primers and Superscript II reverse transcriptase (Invitrogen), according to the manufacturer's instructions). To compensate for variable cDNA yields, the amount of cDNA for each PCR reaction was calibrated by using expression level of the housekeeping gene GADPH as a standard. Amounts of cDNA yielding equivalent amount of GADPH PCR product (at 20 cycles, data not shown) were used for subsequent PCR reactions. cDNAs were amplified using primers from Table 1 for mouse samples and from Table 2 for human samples. All PCR reactions were run for 30 cycles (including those GADPH PCRs which are shown on pictures) and were performed in 20 μl under standard conditions using 1 U of Taq DNA Polimerase Recombinant (Invitrogen). The PCR products were analyzed on a 1.5% agarose gel containing ethidium bromide.

For each RNA sample, RT-PCR without reverse transcriptase was performed to confirm that no genomic DNA was isolated.

TABLE 1

Primers for RT-PCR (mouse samples)

| Gene | Forward primer | Reverse primer | Product size (bp) | Ta, (C) |
|---|---|---|---|---|
| Oct-4 | AGGCCCGGAAGAGAAAGCGAACTA (SEQ ID NO: 1) | TGGGGGCAGAGGAAAGGATACAGC (SEQ ID NO: 2) | 266 | 64 |
| Sox-2 | GTGGAAACTTTTGTCCGAGACC (SEQ ID NO: 3) | TGGAGTGGGAGGAAGAGGTAAC (SEQ ID NO: 4) | 551 | 60 |
| TERT | CTGCGTGTGCGTGCTCTGGAC (SEQ ID NO: 5) | CACGTCAGCAAACAGCTTGTTCTC (SEQ ID NO: 6) | 498 | 64 |
| GADPH | GTGGAGATTGTTGCCATCAACGACC (SEQ ID NO: 7) | GGCTAAGCAGTTGGTGGTGCAGGA (SEQ ID NO: 8) | 393 | 64 |
| Vimentin | CAAGGGTGAGTAGAGAGTTCGGG (SEQ ID NO: 9) | TATAACACTGTTAGGAAAGAGGGTC (SEQ ID NO: 10) | 226 | 60 |
| Nestin | CGGCCCACGCATCCCCCATCC (SEQ ID NO: 11) | CAGCGGCCTTCCAATCTCTGTTCC (SEQ ID NO: 12) | 259 | 64 |
| Brachyury | GCTCATCGGAACAGCTCTCCAACC (SEQ ID NO: 13) | GGAGAACCAGAAGACGAGGACGTG (SEQ ID NO: 14) | 320 | 64 |
| AFP | GTTTTCTGAGGGATGAAACCTATGCC (SEQ ID NO: 15) | CGCCCAAAGCATCACGAGTTTTGG (SEQ ID NO: 16) | 285 | 64 |
| GATA4 | GGCCCCTCATTAAGCCTCAGCGC (SEQ ID NO: 17) | GCAGGACCTGCTGGCGTCTTAGAT (SEQ ID NO: 18) | 250 | 64 |

TABLE 2

Primers for RT-PCR (human samples)

| Gene | Forward primer | Reverse primer | Product size (bp) | Ta, (C) |
|---|---|---|---|---|
| Oct-4 | CGACCATCTGCCGCTTTGAG (SEQ ID NO: 19) | CCCCCTGTCCCCCATTCCTA (SEQ ID NO: 20) | 573 | 61 |
| Nanog | AGCATCCGACTGTAAAGAATCTTCAC (SEQ ID NO: 21) | CGGCCAGTTGTTTTTCTGCCACCT (SEQ ID NO: 22) | 433 | 61 |
| GADPH | GAAGGTGAAGGTCGGAGTCA (SEQ ID NO: 23) | TTCACACCCATGACGAACAT (SEQ ID NO: 24) | 402 | 59 |
| Pax6 | AACAGACACAGCCCTCACAAAC (SEQ ID NO: 25) | CGGGAACTTGAACTGGAACTGAC (SEQ ID NO: 26) | 275 | 61 |
| AFP | CTTTGGGCTGCTCGCTATGA (SEQ ID NO: 27) | TGGCTTGGAAAGTTCGGGTC (SEQ ID NO: 28) | 175 | 59 |
| Brachyury | GAAGGTGGATCTCAGGTAGC (SEQ ID NO: 29) | CATCTCATTGGTGAGCTCCTT (SEQ ID NO: 30) | 251 | 59 |
| Sox1 | CTCACTTTCCTCCGCGTTGCTTCC (SEQ ID NO: 31) | TGCCCTGGTCTTTGTCCTTCATCC (SEQ ID NO: 32) | 849 | 61 |

Immunofluorescence:

For immunofluorescence embryonic cells were fixed in 96-well plate wells by 4% paraformaldehyde, permeabilized by 0.1% Triton-X and blocked by 10% bovine fetal serum (Invitrogen) in 0.1% Tween-20 (Sigma) PBS for 1 hour. Incubation with primary antibody was performed for 1.5 hours at room temperature. Primary antibody against following mouse antigens were used: Oct4 (from BD Biosciences), Sox2, UTF, Nanog, Collagen IV (all from Millipore). Primary antibody against following human antigens were used: Oct4 and Sox2 (both from R@DSystems). Incubation with secondary antibody (Alexa-488- and Alexa 546-labeled, Molecular probes) with DAPI (Molecular probes) was performed for 40 min. Between incubations specimens were washed with 0.1% Tween-20 in PBS three to five times, 10 min for each wash. Specimens were preserved in fluorescence mounting medium (Dako) and observed under fluorescent microscope (Leica).

Chimeric Mice:

After culturing for 95 days (17 passages) on laminin-511 and on laminin-332 mouse embryonic stem cells were expanded on mouse embryonic fibroblasts in presence of LIF and injected into C57BI mice blastocysts (procedure was performed in Karolinska Center for Transgene Technologies, Karolinska institute, Stockholm). Ethical permission #246/05 issued in Sep. 29, 2005 to Karl Tryggvason by the local ethical committee for experimental animal research.

Results

A. Mouse Embryonic Stem Cells Cultured on Laminins-511 or -332 Proliferate and Remain Pluripotent in Absence of Feeders or LIF or Any Other Differentiation Inhibitors On laminin-511 and on laminin-332, mouse embryonic stem cells were found to remain pluripotent in absence of LIF or any other differentiation inhibitor for at least 140 days. See FIG. 1.

Proliferation: Proliferation rate of mouse embryonic stem cells cultured on Laminin-332 and -511 in absence of LIF/MEFs remained stable and same (high) during the whole duration of experiment. See FIG. 1a, b. From day 40 to day 80 doubling time equals 1.2 days.

RT-PCR markers: Pluripotency markers Sox2, Oct4 and proliferation marker Tert were expressed at same extent by mouse embryonic stem cells cultured on laminins-332 and -551 in absence of LIF for 145 days, as pluripotent embryonic stem cells cultured on LIF. See FIG. 2.

Immunofluorescence: The embryonic stem cells expressed pluripotency markers like Oct4, Sox2, UTF1 and Nanog at same extent as embryonic stem cells grown in presence of LIF. See FIG. 3a, b, c, d.

Morphology: Morphology of embryonic stem cells cultured on Laminin-332 and -511 differed significantly from embryonic stem cells cultured on MEFs or gelatin in presence of LIF. Embryonic stem cells cultured on MEFs or gelatine in presence of LIF formed dense clusters with sharp, defined borders. However, embryonic stem cells cultured on laminin-332 and -511 first spread over extracellular matrix coating forming monolayer, and only after that start forming layers. Nonetheless, expression of pluripotency markers Oct4 and Sox2 is not reduced. See FIG. 4.

In vivo (chimeric mice): mouse embryonic stem cells (line GSI-1) after 95 days (17 passages) of culturing on laminin-332 and of laminin-511 in absence of feeder cells or LIF or any other differentiation inhibitors were able to form chimeric mice. To verify that the mouse embryonic stem cells cultured on Laminin-511 or Laminin-332 in absence of feeder cells or differentiation inhibitors were pluripotent, cells maintained for 95 days (17 passages) were injected into mouse blastocysts that were subsequently implanted into pseudopregnant mice. This led to the generation of chimeric mice (FIG. 6) demonstrating that the cells were indeed pluripotent. Mouse embryonic stem cells (line RW4) also generated chimeric mice after 11 passages on laminin-511 or laminin-332 in absence of feeder cells or differentiation inhibitors.

B. Adhesion Correlates with Mouse Embryonic Stem Self-Renewal

It has been found that the ability of certain extracellular matrix components to support mouse embryonic stem cells self-renewal correlates with adhesion. Undifferentiated embryonic stem cells adhere strongly to laminin-332 and laminin-511 (FIGS. 5a and 5c). Average surface area of adherent embryonic stem cells on those laminins is 2.7 times higher than that of weakly attached embryonic stem cells (FIG. 5b). Adhesion of embryonic stem cells to laminin-111, Matrigel™, gelatin was not strong. Weak or no adhesion of embryonic stem cells to laminin-411, poly-D-lysine was observed. Student's two-tailed test reveals that difference between adhesion and surface area for laminin-511 and laminin-332 is statistically different from all other coatings (p-value below 5%).

C. Human Embryonic Stem Cells Cultured on Laminins-511 Proliferate and Remain Pluripotent in Chemically Defined Medium in Absence of Feeders On laminin-511, human embryonic stem cells were found to remain pluripotent in chemically defined medium for at least 105 days (20 passages).

Morphology: Morphology of human embryonic stem cells cultured on Laminin-511 was very similar to that found for human embryonic stem cells cultured on Matrigel™ (Bendall, S. C., Stewart, M. H., Menendez, P., George, D., Vijayaragavan, K., Werbowetski-Ogilvie, T., Ramos-Mejia, V., Rouleau, A., Yang, J., Bossé, M., Lajoie, G. and Bhatia, M. (2007); IGF and FGF cooperatively establish the regulatory stem cell niche of pluripotent human cells in vitro. Nature, Aug. 30, 2007; 448(7157):1015-21) or extracellular-matrix-coated plates (Klimanskaya, I., Chung, Y., Meisner, L., Johnson, J., West, M. D. and Lanza, R. (2005); Human embryonic stem cells derived without feeder cells. Lancet. May 7-13, 2005; 365(9471):1601-1603). See FIG. 7. But, unlike the two coatings mentioned above, recombinant human laminin-511 can be produced according to FDA requirements as a xeno-free, defined and nonimmunogenic compound and subsequently used in clinic.

RT-PCR markers: Pluripotency markers Oct4 and Nanog were expressed at same extent by human embryonic stem cells cultured on laminins-551 in the chemically defined medium for 105 days, as pluripotent embryonic stem cells cultured on human fibroblast foreskin in the conventional medium. See FIG. 8.

Immunofluorescence: Human embryonic stem cells expressed pluripotency markers like Oct4 and Sox2 at same extent as embryonic stem cells grown in conventional environment. See FIG. 9.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A method for enabling proliferation of pluripotent murine embryonic stem cells grown in vitro, comprising: providing an extracellular matrix comprising (i) a laminin selected from the group consisting of recombinant laminin 332 (laminin-5) and recombinant laminin 511 (laminin-10), and (ii) a medium that comprises beta fibroblast growth factor (bFGF); and coating the extracellular matrix with pluripotent murine embryonic stem cells.

2. The method of claim 1, wherein the extracellular matrix is devoid of any differentiation inhibitor.

3. A composition for enabling proliferation of pluripotent stem cells in-vitro for greater than 14 days consisting of a layer of (i) a laminin selected from the group consisting of recombinant laminin 332 (laminin-5) and recombinant laminin 511 (laminin-10) and (ii) beta fibroblast growth factor (bFGF).

* * * * *

SEQUENCE LISTING

<160> NUMBER OF SEQ ID NOS: 32

<210> SEQ ID NO 1
<211> LENGTH: 24
<212> TYPE: DNA
<213> ORGANISM: Mus musculus

<400> SEQUENCE: 1
aggcccggaa gagaaagcga acta                                              24

<210> SEQ ID NO 2
<211> LENGTH: 24
<212> TYPE: DNA
<213> ORGANISM: Mus musculus

<400> SEQUENCE: 2
tgggggcaga ggaaaggata cagc                                              24

<210> SEQ ID NO 3
<211> LENGTH: 22
<212> TYPE: DNA
<213> ORGANISM: Mus musculus

<400> SEQUENCE: 3
gtggaaactt ttgtccgaga cc                                                22

<210> SEQ ID NO 4
<211> LENGTH: 22
<212> TYPE: DNA
<213> ORGANISM: Mus musculus

<400> SEQUENCE: 4
tggagtggga ggaagaggta ac                                                22

<210> SEQ ID NO 5
<211> LENGTH: 21
<212> TYPE: DNA
<213> ORGANISM: Mus musculus

<400> SEQUENCE: 5
ctgcgtgtgc gtgctctgga c                                                 21

<210> SEQ ID NO 6
<211> LENGTH: 24
<212> TYPE: DNA
<213> ORGANISM: Mus musculus

<400> SEQUENCE: 6
cacctcagca aacagcttgt tctc                                              24

<210> SEQ ID NO 7
<211> LENGTH: 25
<212> TYPE: DNA
<213> ORGANISM: Mus musculus

<400> SEQUENCE: 7
gtggagattg ttgccatcaa cgacc                                             25

<210> SEQ ID NO 8
<211> LENGTH: 24
<212> TYPE: DNA

-continued

```
<400> SEQUENCE: 8
ggctaagcag ttggtggtgc agga                                          24

<210> SEQ ID NO 9
<211> LENGTH: 23
<212> TYPE: DNA
<213> ORGANISM: Mus musculus

<400> SEQUENCE: 9
caagggtgag tagagagttc ggg                                           23

<210> SEQ ID NO 10
<211> LENGTH: 25
<212> TYPE: DNA
<213> ORGANISM: Mus musculus

<400> SEQUENCE: 10
tataacactg ttaggaaaga gggtc                                         25

<210> SEQ ID NO 11
<211> LENGTH: 21
<212> TYPE: DNA
<213> ORGANISM: Mus musculus

<400> SEQUENCE: 11
cggcccacgc atcccccatc c                                             21

<210> SEQ ID NO 12
<211> LENGTH: 24
<212> TYPE: DNA
<213> ORGANISM: Mus musculus

<400> SEQUENCE: 12
cagcggcctt ccaatctctg ttcc                                          24

<210> SEQ ID NO 13
<211> LENGTH: 24
<212> TYPE: DNA
<213> ORGANISM: Mus musculus

<400> SEQUENCE: 13
gctcatcgga acagctctcc aacc                                          24

<210> SEQ ID NO 14
<211> LENGTH: 24
<212> TYPE: DNA
<213> ORGANISM: Mus musculus

<400> SEQUENCE: 14
ggagaaccag aagacgagga cgtg                                          24

<210> SEQ ID NO 15
<211> LENGTH: 26
<212> TYPE: DNA
<213> ORGANISM: Mus musculus

<400> SEQUENCE: 15
gttttctgag ggatgaaacc tatgcc                                        26

<210> SEQ ID NO 16
<211> LENGTH: 24
<212> TYPE: DNA
<213> ORGANISM: Mus musculus
```

```
<400> SEQUENCE: 16
cgcccaaagc atcacgagtt ttgg                                            24

<210> SEQ ID NO 17
<211> LENGTH: 23
<212> TYPE: DNA
<213> ORGANISM: Mus musculus

<400> SEQUENCE: 17
ggcccctcat taagcctcag cgc                                             23

<210> SEQ ID NO 18
<211> LENGTH: 24
<212> TYPE: DNA
<213> ORGANISM: Mus musculus

<400> SEQUENCE: 18
gcaggacctg ctggcgtctt agat                                            24

<210> SEQ ID NO 19
<211> LENGTH: 20
<212> TYPE: DNA
<213> ORGANISM: Homo sapiens

<400> SEQUENCE: 19
cgaccatctg ccgctttgag                                                 20

<210> SEQ ID NO 20
<211> LENGTH: 20
<212> TYPE: DNA
<213> ORGANISM: Homo sapiens

<400> SEQUENCE: 20
ccccctgtcc cccattccta                                                 20

<210> SEQ ID NO 21
<211> LENGTH: 26
<212> TYPE: DNA
<213> ORGANISM: Homo sapiens

<400> SEQUENCE: 21
agcatccgac tgtaaagaat cttcac                                          26

<210> SEQ ID NO 22
<211> LENGTH: 24
<212> TYPE: DNA
<213> ORGANISM: Homo sapiens

<400> SEQUENCE: 22
cggccagttg tttttctgcc acct                                            24

<210> SEQ ID NO 23
<211> LENGTH: 20
<212> TYPE: DNA
<213> ORGANISM: Homo sapiens

<400> SEQUENCE: 23
gaaggtgaag gtcggagtca                                                 20

<210> SEQ ID NO 24
<211> LENGTH: 20
<212> TYPE: DNA
<213> ORGANISM: Homo sapiens
```

```
<400> SEQUENCE: 24
ttcacaccca tgacgaacat                                            20

<210> SEQ ID NO 25
<211> LENGTH: 22
<212> TYPE: DNA
<213> ORGANISM: Homo sapiens

<400> SEQUENCE: 25
aacagacaca gccctcacaa ac                                         22

<210> SEQ ID NO 26
<211> LENGTH: 23
<212> TYPE: DNA
<213> ORGANISM: Homo sapiens

<400> SEQUENCE: 26
cgggaacttg aactggaact gac                                        23

<210> SEQ ID NO 27
<211> LENGTH: 20
<212> TYPE: DNA
<213> ORGANISM: Homo sapiens

<400> SEQUENCE: 27
ctttgggctg ctcgctatga                                            20

<210> SEQ ID NO 28
<211> LENGTH: 20
<212> TYPE: DNA
<213> ORGANISM: Homo sapiens

<400> SEQUENCE: 28
tggcttggaa agttcgggtc                                            20

<210> SEQ ID NO 29
<211> LENGTH: 20
<212> TYPE: DNA
<213> ORGANISM: Homo sapiens

<400> SEQUENCE: 29
gaaggtggat ctcaggtagc                                            20

<210> SEQ ID NO 30
<211> LENGTH: 21
<212> TYPE: DNA
<213> ORGANISM: Homo sapiens

<400> SEQUENCE: 30
catctcattg gtgagctcct t                                          21

<210> SEQ ID NO 31
<211> LENGTH: 24
<212> TYPE: DNA
<213> ORGANISM: Homo sapiens

<400> SEQUENCE: 31
ctcactttcc tccgcgttgc ttcc                                       24

<210> SEQ ID NO 32
<211> LENGTH: 24
<212> TYPE: DNA
<213> ORGANISM: Homo sapiens
```

-continued

```
<400> SEQUENCE: 32
tgccctggtc tttgtccttc atcc                                              24
```